United States Patent
Deng et al.

(10) Patent No.: US 8,895,780 B2
(45) Date of Patent: Nov. 25, 2014

(54) PROCESS FOR PREPARING N-H OR N-ALKYL 2-PROPYNAMIDE

(71) Applicants: Da Deng, Shanghai (CN); Juncheng Zheng, Shanghai (CN)

(72) Inventors: Da Deng, Shanghai (CN); Juncheng Zheng, Shanghai (CN)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 14/013,098

(22) Filed: Aug. 29, 2013

(65) Prior Publication Data

US 2014/0066655 A1 Mar. 6, 2014

(30) Foreign Application Priority Data

Sep. 4, 2012 (WO) ............... PCT/CN2012/080954

(51) Int. Cl.
*C07C 231/02* (2006.01)
(52) U.S. Cl.
CPC .................................. *C07C 231/02* (2013.01)
USPC ........................................................ 564/135
(58) Field of Classification Search
CPC .................................................... C07C 231/02
USPC ........................................................ 564/135
See application file for complete search history.

(56) References Cited

U.S. PATENT DOCUMENTS

2014/0066655 A1  3/2014  Deng et al.

FOREIGN PATENT DOCUMENTS

WO          9822429 A1     5/1998

OTHER PUBLICATIONS

Crow et al., "3-Isothiazolone-cis-3-Thiocyanoacrylamide Equilibria". The Journal of Organic Chemistry, vol. 30, No. 8, Aug. 1965, pp. 2660-2665.
Hay et al., "Palladium-Catalyzed Hydroarylation of Propiolamides. A Regio and Stereocontrolled Method for Preparing 3,3-Diarylacrylamides". The Journal of Organic Chemistry, vol. 63, No. 15, Jul. 1998, pp. 5050-5058.
International Search Report and Written Opinion for PCT/EP2013/068095 mailed Nov. 18, 2013.

*Primary Examiner* — Shailendra Kumar
(74) *Attorney, Agent, or Firm* — Michael P. Morris; Mary-Ellen M. Devlin

(57) ABSTRACT

Disclosed is a method for the synthesis of N—H or N-alkyl 2-propynamides useful as intermediate in the manufacture of pharmaceutically active ingredients.

6 Claims, No Drawings

PROCESS FOR PREPARING N—H OR N-ALKYL 2-PROPYNAMIDE

TECHNICAL FIELD

This invention relates to a novel method for the synthesis of N—H or N-alkyl 2-propynamides useful as intermediate in the manufacture of pharmaceutically active ingredients.

BACKGROUND

Several routes to N—H or N-alkyl 2-propynamides are known, but they all suffer from severe drawbacks from a commercial manufacturing point of view. They also do not allow for the control of the quality of the product in a way that is requested for the production of pharmaceutical intermediates. Therefore it is a demand for efficient methods to manufacture N—H or N-alkyl 2-propynamide circumventing these problems.

As very versatile intermediates, different synthetic methods to manufacture derivatives of 2-propynamide have been described in current literature.

J. Org. Chem. 30, 2660 [1965] and J. Org. Chem. 63, 5050 [1998] report the synthesis of propynamides, including propynamide, N-methylpropynamide and N-ethylpropynamide, by the reaction of methyl propiolate with the appropriate amine, at very low temperatures (such as between −30° C. and −60° C., even up to −78° C.) mainly in aqueous methanol. Disadvantageous to this approach is the necessity to carry out this reaction at low temperature between −30° C. and −60° C. to favor the formation of amide product over Michael adduct. Low temperatures are a distinct problem on larger production scale, since they require high investments in cooling equipment and enormous energy consumption to maintain the low temperature, therefore this process is inadequate for commercial manufacture. Further, such very low temperatures may make it difficult to use water as a solvent.

Another amide bond formation strategy involves the use of activated propiolic acid derivatives preformed and/or formed in situ. Examples are propiolic anhydride (J. Chem. Soc. Perkin I 1493 [1975]), propiolyl chloride (J. Org. Chem. 39, 725 [1974] and J. Org. Chem. 63, 9069 [1998]) or mixed anhydride (Synthetic Communications 23, 2003 [1993]). In these approaches the above-mentioned low temperature condition can be avoided. The disadvantage of these methods is however the fact that additional chemical steps have to be performed to generate these activated intermediates and non-aqueous solvents have to be used, since these intermediates are unstable in water. Therefore these methods are from an ecological point of view unfavorable, since a tremendous amount of waste is generated in the case of a commercial application.

An enzymatic approach is described in Tetrahedron 49, 4007 [1993] with a lipase catalyzed reaction between ethyl propiolate and anillines to afford the corresponding amide at 25° C.~60° C. However this reaction has not been shown for the title compounds of this invention and requires the use of special technology as well as highly toxic solvent carbon tetrachloride.

Therefore there is a strong need for a novel process to manufacture N—H or N-alkyl 2-propynamides, which renders the desired product in high quality and good chemical yield, and in an efficient and environmentally friendly manner.

DESCRIPTION OF THE INVENTION

The present invention provides an efficient process for the manufacture of N—H or N-alkyl 2-propynamides of formula (I) as described herein below.

It has been found that the N—H or N-alkyl 2-propynamides of formula (I) can be prepared by reacting methyl or ethyl propiolate of formula (II) with corresponding amine of formula (III) in water, which does not require the use of low temperatures or organic solvents and allows to produce the title compounds of the invention efficiently with good control of the quality (Scheme 1).

Scheme 1. Process for the manufacture of N—H or N-alkyl 2-propynamides according to the invention:

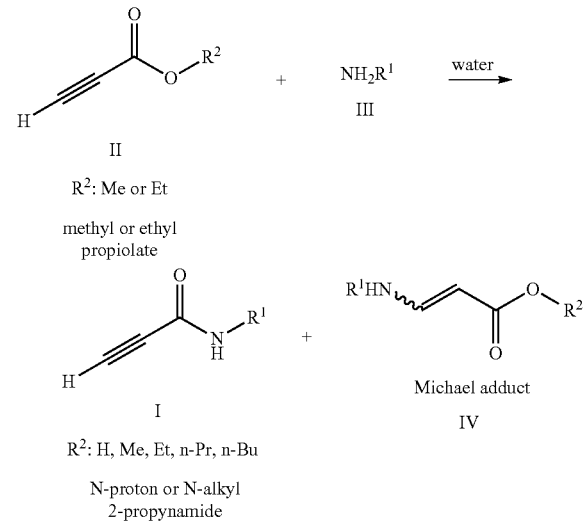

$R^2$: Me or Et methyl or ethyl propiolate $R^2$: H, Me, Et, n-Pr, n-Bu

N-proton or N-alkyl 2-propynamide

Michael adduct

The use of water as process media has been found to be the key to ensure excellent ratio of desired product [N—H or N-alkyl 2-propynamide of formula (I)] to side product [Michael adduct of formula IV] of the reaction between propiolate of formula (II) with amine of formula (III), and consequently leading to product (I) with high purity and also allowing for an environmentally benign process.

The reaction of the invention may be performed at a temperature from −10° C. to 10° C., preferably −3° C. to 5° C., more preferably at 0° C. to 3° C. Higher temperature provides lower selectivity. Lower temperature may slow down the reaction or the reaction may be frozen.

In an embodiment of the process of the invention, the propiolate of formula (II) may be added to the solution of the amine of formula (III) in water, particularly to allow for better temperature, process and quality control.

In a further embodiment of the process of the invention, the amine of formula (III) may be used in an excess amount compared to the propiolate of formula (II), particularly to allow for the completeness of the conversion of propiolate of formula (II) into product of formula (I).

The preferred ratio of propiolate of formula (II) to amine of formula (III) is about 1.0 to about 1.2, more preferably 1.0 to 1.05.

After the reaction is finished, the use of an acid to be added to quench the excess amine of formula (III) may be advantageous. Suitable acids include, but are not limited to, hydrochloric acid and acetic acid, or the like.

Thus, the present invention relates in a first aspect (aspect 1) to a method of preparing N—H or N-alkyl 2-propynamides of formula (I)

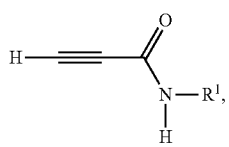

(I)

wherein $R^1$ is hydrogen or $C_{1-4}$-alkyl (e.g. methyl, ethyl, propyl, isopropyl, butyl, isobutyl, sec-butyl, or tert-butyl), particularly methyl, ethyl, n-propyl or n-butyl, said process comprising reacting a propiolic acid ester of formula (II)

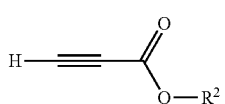

(II)

wherein $R^2$ is $C_{1-2}$-alkyl, particularly methyl or ethyl,
with an amine of the formula (III)

wherein $R^1$ is defined as in formula (I), in a suitable reaction solvent which is water, and at a suitable reaction temperature, which may be from about −10° C. to about 10° C., preferably from about −3° C. to about 5° C., more preferably from about 0° C. to about 3° C., to form a compound of formula (I).

As further embodimental aspects of the invention, the following aspects 2-7 may be mentioned:

2. The method according to above aspect 1, wherein the reaction temperature is such that the reaction effectively proceeds, the reaction medium is in liquid state and/or the portion of Michael adduct is substantially reduced, such as e.g. below 15 mol %, below 10 mol % or even below 5 mol %, preferably below 1 mol %, more preferably below 0.5 mol % formed or comprised in the product.

3. The method according to above aspect 1 or 2, wherein $R^1$ is $C_{1-4}$-alkyl (e.g. methyl, ethyl, propyl, isopropyl, butyl, isobutyl, sec-butyl, or tert-butyl), particularly methyl, ethyl, n-propyl or n-butyl.

4. The method according to above aspect 1, 2 or 3, wherein $R^2$ is methyl.

5. The method according to above aspect 1, 2 or 3, wherein $R^2$ is ethyl.

6. The method according to any one aspect 1 to 5, wherein the propiolic acid ester of formula (II) and the amine of formula (III) are used in a ratio of about 1.0 to about 1.2, preferably 1.0 to 1.05.

7. The method according to any one aspect 1 to 6, wherein the propiolic acid ester of formula (II) is added to a solution of the amine of formula (III) in water.

The reactants used in the synthetic schemes described below may be obtained either as described herein, or if not described herein, are themselves either commercially available or may be prepared from commercially available materials by methods known in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by Gas Chromatography (GC) or Thin Layer Chromatography, if desired.

EXAMPLES

In order that this invention be more fully understood, the following examples are set forth. These examples are for the purpose of illustrating preferred embodiments of this invention, and are not to be construed as limiting the scope of the invention in any way.

Example 1

Propynamide: To a solution of 30 mL of water and 7.15 g (105 mmol) ammonia (25-28 wt % in water) is added dropwise 8.4 g (100 mmol) methyl propiolate at 0° C. for 30 minutes. The mixture was stirred for 2 h at 0° C., then acetic acid (2 mL) was added. The mixture was stirred for another 10 minutes and saturated with NaCl, followed by extraction with ethyl acetate (3×40 mL). The combined organic phase was washed with saturated aqueous solution of NaH—CO$_3$ (20 mL), dried over Na$_2$SO$_4$, and removed by rotary evaporation to give product (5.0 g, yield 72%, purity 99% by GC).

$^1$H NMR (400 MHz, DMSO-d6) δ 8.07 (1H, s), 7.61 (1H, s), 4.05 (1H, s).

Example 2

N-Methyl 2-propynamide: To a solution of 30 mL of water and 13.1 g (105 mmol) methylamine aqueous solution (25-30 wt %) is added dropwise 8.4 g (100 mmol) methyl propiolate at 0° C. for 30 minutes. The mixture was stirred for 2 h at 0° C., then acetic acid (2 mL) was added. The mixture was stirred for another 10 minutes and saturated with NaCl, followed by extraction with ethyl acetate (3×40 mL). The combined organic phase was washed with saturated aqueous solution of NaHCO$_3$ (20 mL), dried over Na$_2$SO$_4$, and removed by rotary evaporation to give product (5.6 g, yield 68%, purity 96% by GC).

$^1$H NMR (400 MHz, DMSO-d6) δ 8.62 (1H, s), 4.09 (1H, s), 2.60 (3H, d, J=4.8 Hz).

Example 3

N-Ethyl 2-propynamide: To a solution of 30 mL of water and 7.28 g (105 mmol) ethylamine aqueous solution (65-70 wt %) is added dropwise 8.4 g (100 mmol) methyl propiolate at 0° C. for 30 minutes. The mixture was stirred for 2 h at 0° C., then acetic acid (2 mL) was added. The mixture was stirred for another 10 minutes and saturated with NaCl, followed by extraction with ethyl acetate (3×20 mL). The combined organic phase was washed with saturated aqueous solution of NaHCO$_3$ (20 mL), dried over Na$_2$SO$_4$, and removed by rotary evaporation to give product (8.9 g, yield 92%, purity 98% by GC).

$^1$H NMR (400 MHz, DMSO-d6) δ 8.67 (1H, s), 4.05 (1H, s), 3.09 (2H, m), 1.01 (3H, t, J=7.3 Hz).

Example 4

N-Propyl 2-propynamide: To a solution of 30 mL of water and 5.91 g (100 mmol) n-propylamine is added dropwise 8.4 g (100 mmol) methyl propiolate at 0° C. for 30 minutes. The mixture was stirred for 2 h at 0° C., then acetic acid (2 mL) was added. The mixture was stirred for another 10 minutes and saturated with NaCl, followed by extraction with ethyl acetate (3×20 mL). The combined organic phase was washed with saturated aqueous solution of NaH—CO₃ (20 mL), dried over Na₂SO₄, and removed by rotary evaporation to give product (10.3 g, yield 93%, purity 98% by GC).

¹H NMR (400 MHz, DMSO-d6) δ 8.68 (1H, s), 4.06 (1H, s), 3.03 (2H, dd, J=6.9, 12.9 Hz), 1.41 (2H, m), 0.84 (3H, t, J=7.3 Hz).

Example 5

N-Butyl 2-propynamide: To a solution of 30 mL of water and 7.3 g (100 mmol) n-Butylamine is added dropwise 8.4 g (100 mmol) methyl propiolate at 0° C. for 30 minutes. The mixture was stirred for 2 h at 0° C., then acetic acid (2 mL) was added. The mixture was stirred for another 10 minutes and saturated with NaCl, followed by extraction with ethyl acetate (3×20 mL). The combined organic phase was washed with saturated aqueous solution of NaHCO₃ (20 mL), dried over Na₂SO₄, and removed by rotary evaporation to give product (12.0 g, yield 96%, purity 96% by GC).

¹H NMR (400 MHz, DMSO-d6) δ 8.65 (1H, s), 4.04 (1H, s), 3.06 (2H, dd, J=6.7, 13.0 Hz), 1.42 (2H, m), 1.27 (2H, m), 0.88 (3H, t, J=7.3 Hz).

Example 6

Propynamide: To a solution of 30 mL of water and 9.19 g (135 mmol) ammonia (25-28 wt %) is added dropwise 9.81 g (100 mmol) ethyl propiolate at 0° C. for 30 minutes. The mixture was stirred for 5 h at 0° C., then acetic acid (3 mL) was added. The mixture was stirred for another 10 minutes and saturated with NaCl, followed by extraction with ethyl acetate (3×40 mL). The combined organic phase was washed with saturated aqueous solution of NaHCO₃ (20 mL), dried over Na₂SO₄, and removed by rotary evaporation to give product (5.0 g, yield 72%, purity 99% by GC).

¹H NMR (400 MHz, DMSO-d6) δ 8.07 (1H, s), 7.61 (1H, s), 4.05 (1H, s).

Example 7

N-Methyl 2-propynamide: To a solution of 30 mL of water and 13.1 g (105 mmol) methylamine (25-30 wt %) is added dropwise 9.81 g (100 mmol) ethyl propiolate at 0° C. for 30 minutes. The mixture was stirred for 2 h at 0° C., then acetic acid (2 mL) was added. The mixture was stirred for another 10 minutes and saturated with NaCl, followed by extraction with ethyl acetate (3×40 mL). The combined organic phase was washed with saturated aqueous solution of NaHCO₃ (20 mL), dried over Na₂SO₄, and removed by rotary evaporation to give product (5.8 g, yield 70%, purity 97% by GC).

¹H NMR (400 MHz, DMSO-d6) δ 8.62 (1H, s), 4.09 (1H, s), 2.60 (3H, d, J=4.8 Hz).

Example 8

N-Ethyl 2-propynamide: To a solution of 30 mL of water and 7.28 g (105 mmol) ethylamine (65-70 wt %) is added dropwise 9.81 g (100 mmol) ethyl propiolate at 0° C. for 30 minutes. The mixture was stirred for 2 h at 0° C., then acetic acid (2 mL) was added. The mixture was stirred for another 10 minutes and saturated with NaCl, followed by extraction with ethyl acetate (3×20 mL). The combined organic phase was washed with saturated aqueous solution of NaH—CO₃ (20 mL), dried over Na₂SO₄, and removed by rotary evaporation to give product (9.0 g, yield 93%, purity 94% by GC).

¹H NMR (400 MHz, DMSO-d6) δ 8.67 (1H, s), 4.05 (1H, s), 3.09 (2H, m), 1.01 (3H, t, J=7.3 Hz).

Example 9

N-Propyl 2-propyamide: To a solution of 30 mL of water and 6.2 g (105 mmol) n-propylamine is added dropwise 9.8 g (100 mmol) ethyl propiolate at 0° C. for 30 minutes. The mixture was stirred for 5 h at 0° C., then acetic acid (2 mL) was added. The mixture was stirred for another 10 minutes and saturated with NaCl, followed by extraction with ethyl acetate (3×20 mL). The combined organic phase was washed with saturated aqueous solution of NaHCO₃ (20 mL), dried over Na₂SO₄, and removed by rotary evaporation to give product (10.5 g, yield 95%, purity 84% by GC).

¹H NMR (400 MHz, DMSO-d6) δ 8.68 (1H, s), 4.06 (1H, s), 3.03 (2H, dd, J=6.9, 12.9 Hz), 1.41 (2H, m), 0.84 (3H, t, J=7.3 Hz).

Example 10

N-Butyl 2-propynamide: To a solution of 30 mL of water and 7.68 g (105 mmol) n-Butylamine is added dropwise 9.8 g (100 mmol) ethyl propiolate at 0° C. for 30 minutes. The mixture was stirred for 2 h at 0° C., then acetic acid (2 mL) was added. The mixture was stirred for another 10 minutes and saturated with NaCl, followed by extraction with ethyl acetate (3×20 mL). The combined organic phase was washed with saturated aqueous solution of NaHCO₃ (20 mL), dried over Na₂SO₄, and removed by rotary evaporation to give product (12.0 g, yield 95%, purity 69% by GC).

¹H NMR (400 MHz, DMSO-d6) δ 8.65 (1H, s), 4.04 (1H, s), 3.06 (2H, dd, J=6.7, 13.0 Hz), 1.42 (2H, m), 1.27 (2H, m), 0.88 (3H, t, J=7.3 Hz).

What is claimed is:

1. A method of preparing N—H or N-alkyl 2-propynamides of formula (I)

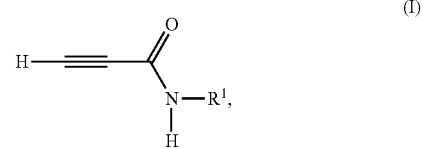

wherein
R¹ is hydrogen or $C_{1-4}$-alkyl,
said process comprising reacting a propiolic acid ester of formula (II)

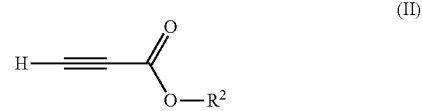

wherein
R² is $C_{1-2}$-alkyl,
with an amine of the formula (III)

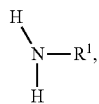

wherein
R¹ is defined as in formula (I),
in water, and at a reaction temperature from of about −10° C. to about 10° C. to form a compound of formula (I).

2. The method according to claim 1, wherein $R^1$ is $C_{1-4}$-alkyl.

3. The method according to claim 1, wherein $R^2$ is methyl.

4. The method according to claim 1, wherein $R^2$ is ethyl.

5. The method according to claim 1, wherein the propiolic acid ester of formula (II) and the amine of formula (III) are used in a ratio of about 1.0 to about 1.2.

6. The method according to claim 1, wherein the propiolic acid ester of formula (II) is added to a solution of the amine of formula (III) in water.

* * * * *